United States Patent
Gerhard

(10) Patent No.: US 9,618,387 B2
(45) Date of Patent: Apr. 11, 2017

(54) METHOD FOR DETERMINING THE PHASE ANGLE AND/OR THE THICKNESS OF A CONTAMINATION LAYER AT AN OPTICAL ELEMENT AND EUV LITHOGRAPHY APPARATUS

(71) Applicant: Carl Zeiss SMT GmbH, Oberkochen (DE)

(72) Inventor: Michael Gerhard, Aalen (DE)

(73) Assignee: Carl Zeiss SMT GmbH, Oberkochen (DE)

(*) Notice: Subject to any disclaimer, the term of this patent is extended or adjusted under 35 U.S.C. 154(b) by 0 days.

(21) Appl. No.: 14/808,637

(22) Filed: Jul. 24, 2015

(65) Prior Publication Data
US 2016/0025554 A1  Jan. 28, 2016

Related U.S. Application Data

(63) Continuation of application No. PCT/EP2013/074170, filed on Nov. 19, 2013.
(Continued)

(30) Foreign Application Priority Data

Jan. 25, 2013 (DE) .......... 10 2013 201 193

(51) Int. Cl.
*G03B 27/54* (2006.01)
*G01J 1/02* (2006.01)
(Continued)

(52) U.S. Cl.
CPC ............ *G01J 1/0238* (2013.01); *B82Y 10/00* (2013.01); *G01B 11/06* (2013.01);
(Continued)

(58) Field of Classification Search
CPC ..... G01J 1/0238; G01J 1/429; G01B 11/0625; B82Y 10/00; G03F 7/7085; G03F 7/70908; G03F 7/70958
(Continued)

(56) References Cited

U.S. PATENT DOCUMENTS 5,393,980 A  2/1995 Yost et al.
2002/0083409 A1  6/2002 Hamm
(Continued)

FOREIGN PATENT DOCUMENTS

DE  10061248 A1  6/2002
DE  10209493 B4  3/2007
(Continued)

OTHER PUBLICATIONS

International Search Report and Written Opinion in counterpart International Application No. PCT/EP2013/074170, mailed Jul. 1, 2014.
(Continued)

*Primary Examiner* — Hung Henry Nguyen
(74) *Attorney, Agent, or Firm* — Edell, Shapiro & Finnan, LLC

(57) ABSTRACT

A method and associated EUV lithography apparatus for determining the phase angle at a free interface (17) of an optical element (13) provided with a multilayer coating (16) that reflects EUV radiation and/or for determining the thickness (d) of a contamination layer (26) formed on the multilayer coating (16). The multilayer coating (16) is irradiated with EUV radiation, a photocurrent ($I_P$) generated during the irradiation is measured, and the phase angle at the free interface (17) and/or the thickness (d) of the contamination layer (26) is determined on the basis of a predefined relationship between the phase angle and/or the thickness (d) and the measured photocurrent ($I_P$). The measured photo-
(Continued)

current ($I_P$) is generated from the entire wavelength and angle-of-incidence distribution of the EUV radiation impinging on the multilayer coating (16).

6 Claims, 3 Drawing Sheets

Related U.S. Application Data

(60) Provisional application No. 61/756,640, filed on Jan. 25, 2013.

(51) Int. Cl.
*G01B 11/06* (2006.01)
*G01N 21/94* (2006.01)
*G03F 7/20* (2006.01)
*G21K 1/06* (2006.01)
*G01N 21/41* (2006.01)
*G01N 21/84* (2006.01)
*B82Y 10/00* (2011.01)
*G01J 1/42* (2006.01)

(52) U.S. Cl.
CPC .......... *G01B 11/0616* (2013.01); *G01J 1/429* (2013.01); *G01N 21/41* (2013.01); *G01N 21/8422* (2013.01); *G01N 21/94* (2013.01); *G03F 7/20* (2013.01); *G03F 7/7085* (2013.01); *G03F 7/70141* (2013.01); *G03F 7/70591* (2013.01); *G03F 7/70858* (2013.01); *G03F 7/70908* (2013.01); *G03F 7/70916* (2013.01); *G03F 7/70958* (2013.01); *G21K 1/062* (2013.01)

(58) Field of Classification Search
USPC .................. 355/67; 250/504 R; 356/218
See application file for complete search history.

(56) References Cited

U.S. PATENT DOCUMENTS

| | | | |
|---|---|---|---|
| 2006/0192158 A1 | 8/2006 | Wedowski et al. | |
| 2007/0008517 A1* | 1/2007 | Fomenkov | B82Y 10/00 356/218 |
| 2007/0285643 A1* | 12/2007 | Wedowski | G01B 11/0625 355/67 |
| 2011/0079737 A1* | 4/2011 | Scholz | B82Y 10/00 250/504 R |
| 2013/0148200 A1 | 6/2013 | Ehm et al. | |

FOREIGN PATENT DOCUMENTS

| | | |
|---|---|---|
| DE | 102006029799 A1 | 1/2008 |
| DE | 102006044591 A1 | 4/2008 |
| EP | 0987601 A2 | 3/2000 |
| WO | 2005091076 A2 | 9/2005 |
| WO | 2008034582 A2 | 3/2008 |

OTHER PUBLICATIONS

Office Action in corresponding German Application No. 102013201193.8, dated Jun. 25, 2013, along with an English translation.

\* cited by examiner

METHOD FOR DETERMINING THE PHASE ANGLE AND/OR THE THICKNESS OF A CONTAMINATION LAYER AT AN OPTICAL ELEMENT AND EUV LITHOGRAPHY APPARATUS

CROSS-REFERENCE TO RELATED APPLICATIONS

This application is a Continuation of International Application No. PCT/EP2013/074170, filed on Nov. 19, 2013, which claims benefit under 35 U.S.C. §119(e) to U.S. Provisional Application No. 61/756,640, filed Jan. 25, 2013, and which claims priority under 35 U.S.C. §119(a) to German Patent Application No. 10 2013 201 193.8, also filed on Jan. 25, 2013. The disclosures of all three related applications are considered part of and are incorporated by reference into the disclosure of the present application in their respective entireties.

FIELD AND BACKGROUND OF THE INVENTION

The invention relates to a method for determining the phase angle at a free interface of an optical element provided with a multilayer coating that reflects EUV radiation and/or for determining the thickness of a contamination layer formed on the multilayer coating. The invention also relates to an EUV lithography apparatus, comprising: at least one optical element having a substrate and a multilayer coating that reflects EUV radiation, wherein electrical contact can be made with the optical element for deriving a photocurrent generated during the irradiation with EUV radiation.

At optical elements having a multilayer coating for reflecting EUV radiation, standing waves form during the irradiation. On the basis of the phase angle of such a standing wave at the free interface with respect to the (vacuum) environment, it is possible to draw conclusions about the multilayer coating or about the constitution thereof. Since optical elements that reflect EUV radiation are typically operated in a vacuum environment in a residual gas atmosphere in which the occurrence of contaminating gaseous substances cannot completely be avoided, a contamination layer often forms at the optical elements. On the basis of the phase angle of the standing wave, it is also possible to draw conclusions about the thickness of such a contamination layer that has deposited on the multilayer coating.

The number of charges liberated during the irradiation with EUV radiation as a result of the photoelectric effect at the optical element or the coating varies depending on the phase of the standing wave at the free interface of the optical element. On the basis of the intensity of the photoelectron current (hereinafter for short: photocurrent), it is thus possible to draw conclusions about the phase angle at the free interface and/or about the thickness of the contamination layer.

WO 2005/091076 A2 has disclosed a method for determining the thickness of a capping layer system on a multilayer coating that reflects EUV radiation. Determining the thickness of the capping layer system involves firstly determining a first phase shift of a standing electromagnetic wave at the free interface of the multilayer coating. For this purpose, both the reflectivity and the photocurrent are measured in a wavelength-resolved manner during the irradiation of the free interface with EUV radiation and the first phase shift is determined on the basis of the profile of the photocurrent in the range of maximum reflectivity. A comparison with an already known profile of the photocurrent in the case of a second phase shift of the corresponding standing wave is also performed in order to determine a thickness difference or the thickness of the capping layer system on the basis of the difference between the first and second phase shifts. Instead of a wavelength-resolved measurement of the reflectivity and of the photocurrent, an angle-resolved measurement can also be effected. The measurement of the reflectivity and of the photocurrent can, if appropriate, also be effected for specific combinations of wavelengths and angles of the incident EUV radiation.

In WO2005/091076 A2, photoelectrons ejected from the multilayer coating by the EUV radiation are trapped by an electron trapping device, which can be designed e.g. as a vacuum wall, plate or wire grid. The current generated by the trapped electrons is detected by an ammeter. A ring, a cylinder or a grid can be used for generating a defined electric field between the multilayer coating and the electron trapping device.

An EUV lithography apparatus provided with a detection device for photoelectrons has also been disclosed by DE 102 09 493 B4, wherein use is made of an electron trap for trapping the electrons, which electron trap can be designed e.g. as a detection grid or as a detection ring. The current generated by the trapped electrons is detected by an ammeter. The gas composition of the residual gas atmosphere of the EUV lithography apparatus is regulated on the basis of the measured photocurrent.

EP 0 987 601 A2 describes an exposure apparatus in which a detection device is provided adjacent to a reflective surface in order to detect electrons generated during the irradiation of the reflective surface with X-ray radiation as a result of the photoelectric effect. On the basis of the quantity of photoelectrically generated electrons, the radiation dose occurring during the irradiation with EUV radiation at the mask can be determined and the radiation power of the X-ray radiation can be limited. The detection device can have a grounded ammeter or a voltmeter. The ammeter can be connected to a reflective multilayer coating of a mirror of the exposure apparatus via an electrical cable.

SUMMARY

It is an object of the invention to develop a method of the type mentioned in the introduction such that it can be used during the operation of an EUV lithography apparatus. A further object is to provide an EUV lithography apparatus which simplifies the implementation of this method.

These and other objects are addressed by a method of the type mentioned in the introduction, comprising: irradiating the multilayer coating with EUV radiation, measuring a photocurrent generated during the irradiation, and determining the phase angle at the free interface and/or the thickness of the contamination layer on the basis of a predefined relationship between the phase angle and/or the thickness and the measured photocurrent, wherein the measured photocurrent is generated from the entire wavelength and angle-of-incidence distribution of the EUV radiation impinging on the multilayer coating.

This aspect of the invention proposes, instead of the wavelength-resolved or angle-resolved measurement of the photocurrent as described in WO 2005/091076 A2, measuring the photocurrent as an integral over the wavelength band used during the irradiation and over the angles of incidence used during the irradiation and directly determining the phase at the free interface and/or the thickness of the contamination layer in accordance with a predefined photocurrent/phase curve and/or photocurrent/thickness curve in accordance with the measured photocurrent. The determination of the reflectivity of the optical element, as described in WO 2005/091076 A2, is not necessary for this purpose.

The determination of the phase angle is advantageous primarily if no contamination layer is present at the optical element, such that the free interface of the optical element corresponds to the top side of the multilayer coating, wherein the topmost layer of the multilayer coating is typically formed by a capping layer for protecting the multilayer coating e.g. against oxidation. If no contamination layer is present, on the basis of the phase angle it is possible to draw conclusions about the state of the multilayer coating or about the variation of its state during the service life, for example whether the multilayer coating has compacted during the irradiation or a diffusion of the materials of the individual layers of the multilayer coating has taken place. Moreover, as a result of the determination of the phase angle at a plurality of optical elements e.g. of a projection system of an EUV lithography apparatus, it is possible to make a statement about the (relative) phase of the EUV radiation at the individual reflective elements. In order to remove a contamination layer possibly present from the optical element before the phase angle is determined, the optical element can be cleaned e.g. with the aid of a cleaning gas, in particular with the aid of activated hydrogen. However, the photocurrent should be measured at a point in time at which there is no or only a very small content of activated hydrogen in the residual gas atmosphere surrounding the optical element, since said activated hydrogen forms free radicals (H+) which can corrupt the measurement result.

For measuring the photocurrent it is possible to use an electron trap, as described in the documents cited in the introduction. It is more advantageous (and primarily saves more space) if the photocurrent is taken directly from the optical element, more precisely from the multilayer coating. For this purpose, an electrically conductive, e.g. metallic, layer can be arranged between the substrate and the multilayer coating of the optical element, it being possible to make electrical contact with said layer in order to derive the photocurrent, as is known from WO 2008/034582, which is incorporated by reference in the content of this application. If appropriate, it is also possible to make electrical contact with the free interface of the optical element directly outside the optical used region.

In one variant, the predefined relationship between the phase angle at the free interface and the photocurrent and/or between the thickness of the contamination layer and the photocurrent is calibrated during a time period in which the optical element is not irradiated with EUV radiation at wavelengths that are reflected by the multilayer coating. As has been explained further above, the measured sample current depends on the intensity of the impinging EUV radiation, which fluctuates possibly in a time-dependent manner in the case of a predefined illumination setting and a predefined mask structure. In order that a contact resistance which possibly varies over the service life of the optical element and occurs when the sample current is derived is not identified as a change in the phase angle and/or the layer thickness, the relationship between the number of generated photoelectrons and the measured photocurrent should be checked from time to time or at regular intervals and, if appropriate, the corresponding photocurrent/phase curves and/or photocurrent/thickness curves should be adapted. It has proved to be advantageous if the calibration is carried out in operating pauses of the EUV lithography apparatus in which no wafer exposure takes place.

In one variant, a number of charges predefined by a charge standard are fed to the optical element during calibration. The charge standard used can be, for example, a calibrated capacitor whose capacitance defines the predefined number of charges. The national calibration institutes offer complete solutions for generating defined charge packets or a defined number of charges. The calibration generally requires a further contact location, which should be situated on the opposite side relative to the contact location for tapping off the sample current.

In a further variant, during calibration, the optical element is irradiated with calibration radiation at wavelengths that are not reflected at the multilayer coating and are therefore independent of the phase angle of the multilayer. The calibration radiation can be generated with the aid of a calibration radiation source which is switched on for a predefined time interval, wherein the intensity of the calibration radiation generated by the calibration radiation source at the free interface is likewise known or can be determined on the basis of simulation calculations or can be measured during the production of the EUV lithography apparatus. The predefined dose of the calibration radiation generated by the calibration radiation source at the free surface likewise generates a predefined number of charges, such that the ratio of photons to sample current can be checked.

In one advantageous development, the wavelengths of the calibration radiation lie just outside the range in which a significant reflection of the EUV radiation takes place, i.e. in the case of a maximum reflectivity of the multilayer coating at a wavelength of approximately 13.5 nm in the wavelength range of between 9 nm and 11 nm or in the wavelength range of between 14 nm and 16 nm. Both wavelength ranges lie outside the wavelength range that is reflected by the reflective multilayer coating, which is typically designed for the reflection of a central wavelength or operating wavelength of approximately 13.5 nm, wherein the reflectivity typically falls rapidly to zero even in the case of small deviations from the central wavelength, such that already at wavelengths below 11 nm or above 14 nm there is no longer any appreciable reflection. The wavelengths of the calibration radiation can also be very far away from the operating wavelength or the wavelength of maximum reflection, e.g. in the UV range, in particular at wavelengths of between 190 nm and 450 nm.

Within the meaning of this application, reflection by the multilayer coating is understood to mean the interference or Bragg reflection at alternating high and low refractive index individual layers of the multilayer coating which generate the standing wave at the optical element. If appropriate, at the material of a capping layer provided at the multilayer coating or, if appropriate, the contamination layer, part of the calibration radiation can be reflected by conventional refraction at the free interface.

Besides the phase angle and/or the thickness of the contamination layer, the intensity of the measured photocurrent is also dependent on the intensity of the EUV radiation at the free interface of the optical element. The intensity of the EUV radiation in an EUV lithography apparatus, in particular in a projection optical unit of an EUV lithography apparatus, is dependent on the chosen illumination settings (e.g. dipole illumination, annular illumination, etc.) and on the mask arranged in the beam path upstream of the projection optical unit, or the structure to be imaged that is provided on said mask. Typically, therefore, a dedicated photocurrent/phase curve and/or photocurrent/thickness curve are/is used in each case for different illumination settings. Accordingly, in each case different photocurrent/phase curves and/or photocurrent/thickness curves can also be provided for different types of masks or mask structures. An evaluation device can select a suitable characteristic curve or curve depending on the illumination settings and/or on the chosen mask structure.

In one variant, the spatial distribution of the EUV radiation impinging on the multilayer coating is varied for the location-dependent determination of the phase angle at the free interface and/or the thickness of the contamination layer. The phase angle and/or the thickness of the contamination layer can vary in a location-dependent manner along the free interface. In order to be able to detect such location-dependent variations, use can be made of the fact that the location-dependent intensity distribution at the free interface varies depending on the illumination settings and on the mask structure used. The location-dependent intensity distribution on the optical element can be changed through targeted variation of the illumination settings and/or by choosing different exposure masks. By using the thicknesses and/or phase angles determined for different intensity distributions, it is possible to determine the phase angle and/or the thickness—within certain limits—in a location-dependent manner. By way of example, during the annular illumination of an optical element arranged in proximity to a pupil plane, it is possible to determine the phase angle in a ring-shaped region at the free interface in a targeted manner. An absolute calibration of the photocurrent is not necessary in the relative location-dependent measurement.

In one advantageous variant, a charge amplifier is used for measuring the photocurrent generated during the irradiation. A charge amplifier is a charge-voltage converter which converts the input charge arriving at a signal input into a voltage value proportional to the input charge at the signal output. The proportionality constant between input charge and output voltage determines the gain of the charge amplifier. The inventor has recognized that, in the case of the present use in EUV lithography apparatuses, only very few charges or electrons are generated as a result of the photoelectric effect. The charge amplifier makes it possible to significantly increase the measurement accuracy when determining the phase angle and/or the thickness of the contamination layer in comparison with the use e.g. of an ammeter (without a charge amplifier). Moreover, the output signal of the charge amplifier, particularly if the latter has a low output impedance, can be transmitted in a manner free of interference and without problems even over relatively large distances.

A further aspect of the invention relates to an EUV lithography apparatus of the type mentioned in the introduction which has a charge amplifier that is in contact with the optical element for deriving the photocurrent. The charge amplifier can be connected to an electrically conductive layer in particular via a cable, said layer being formed for deriving the photocurrent between the multilayer coating and the substrate, as explained in WO 2008/034582 described further above. However, it is also possible, if appropriate, to make contact e.g. laterally with electrically conductive individual layers of the multilayer coating or the free interface. The corresponding layer can project in particular laterally beyond the rest of the layer stack for the purpose of making electrical contact.

In one embodiment, the charge amplifier is arranged at a distance of less than 150 cm, preferably of less than 50 cm, from the optical element. In particular, the charge amplifier can be arranged in the region of a mount or holder for the optical element. The arrangement of the charge amplifier in proximity to the optical element has proved to be advantageous for avoiding conduction losses and minimizing electromagnetic noise. The charge amplifier can be arranged within the vacuum environment in which the optical element is also situated, but it is also possible to arrange the charge amplifier outside the vacuum environment and to lead the line or the cable out of the vacuum environment. In this way, the exchange or maintenance of the charge amplifier is simplified, but this advantage is bought at the expense of a considerable increase in the electromagnetic noise.

In one embodiment, the EUV lithography apparatus additionally comprises a measuring device for measuring the photocurrent on the basis of an output voltage supplied by the charge amplifier. The measuring device can be designed as a voltmeter, for example, which measures the output voltage of the charge amplifier, said output voltage being proportional to the photocurrent. The measuring device is typically connected to the charge amplifier via a measuring line. The required supply energy is typically fed to the charge amplifier by a separate supply line.

In one development, the measuring device is connected to a pulsed EUV light source of the EUV lithography apparatus in order to read out the output voltage supplied by the charge amplifier synchronously with the pulses of the EUV light source. Since the EUV light source of the EUV lithography apparatus is operated in a pulsed manner, the photocurrent generated during the irradiation is also pulsed, that is to say that the output voltage generated at the signal output of the charge amplifier is also typically pulsed. Since only the photocurrent generated by the EUV radiation, but not the photocurrent generated in the pulse intermissions, is intended to be evaluated, it is advantageous to synchronize the read-out of the voltage pulses generated by the charge amplifier with the EUV light source. In this case, the synchronization can be effected in the manner of the so-called lock-in method, that is to say that the EUV light source supplies a reference signal or a trigger signal for the read-out of the voltage pulses.

In one embodiment, the EUV lithography apparatus additionally comprises an evaluation device, which is designed to determine the phase angle at a free interface of the optical element and/or the thickness of a contamination layer formed on the multilayer coating on the basis of a predefined relationship between the phase angle and/or the thickness and the measured photocurrent, wherein the measured photocurrent is generated from the entire wavelength and angle-of-incidence distribution of the EUV radiation impinging on the multilayer coating. As described further above in connection with the method, it is possible to determine the phase angle on the basis of a photocurrent/phase characteristic curve and/or the thickness of the contamination layer on the basis of the photocurrent/thickness characteristic curve.

In a further embodiment, the EUV lithography apparatus comprises a charge standard for feeding a predefined number of charges to the optical element. The charge standard can be a (calibrated) capacitor, for example.

In a further embodiment, the EUV lithography apparatus comprises a calibration light source for irradiating the optical element with calibration radiation at wavelengths that are not reflected by the multilayer coating. The calibration radiation can be for example radiation which is generated by a calibration light source in a wavelength range of between 9 nm and 11 nm or between 14 nm and 16 nm. Alternatively or additionally, it is also possible to use radiation in the UV range or in the visible wavelength range, for example at wavelengths of between approximately 190 nm and 450 nm, which can be generated for example by laser diodes or by a broadband light source. The use of calibration radiation in the UV range or in the visible range is advantageous since this radiation can be fed to the optical element via an optical fiber. Feeding with free beam propagation is also possible.

Further features and advantages of the invention are evident from the following description of exemplary embodiments of the invention, with reference to the figures of the drawing, which show details essential to the invention, and from the claims. The individual features can be realized in each case individually by themselves or as a plurality in arbitrary combination in a variant of the invention.

BRIEF DESCRIPTION OF THE DRAWINGS

Exemplary embodiments are illustrated in the schematic drawing and are explained in the following description. In the figures.

DETAILED DESCRIPTION

In the following description of the drawings, identical reference signs are used for identical or functionally identical components.

Figure 1:
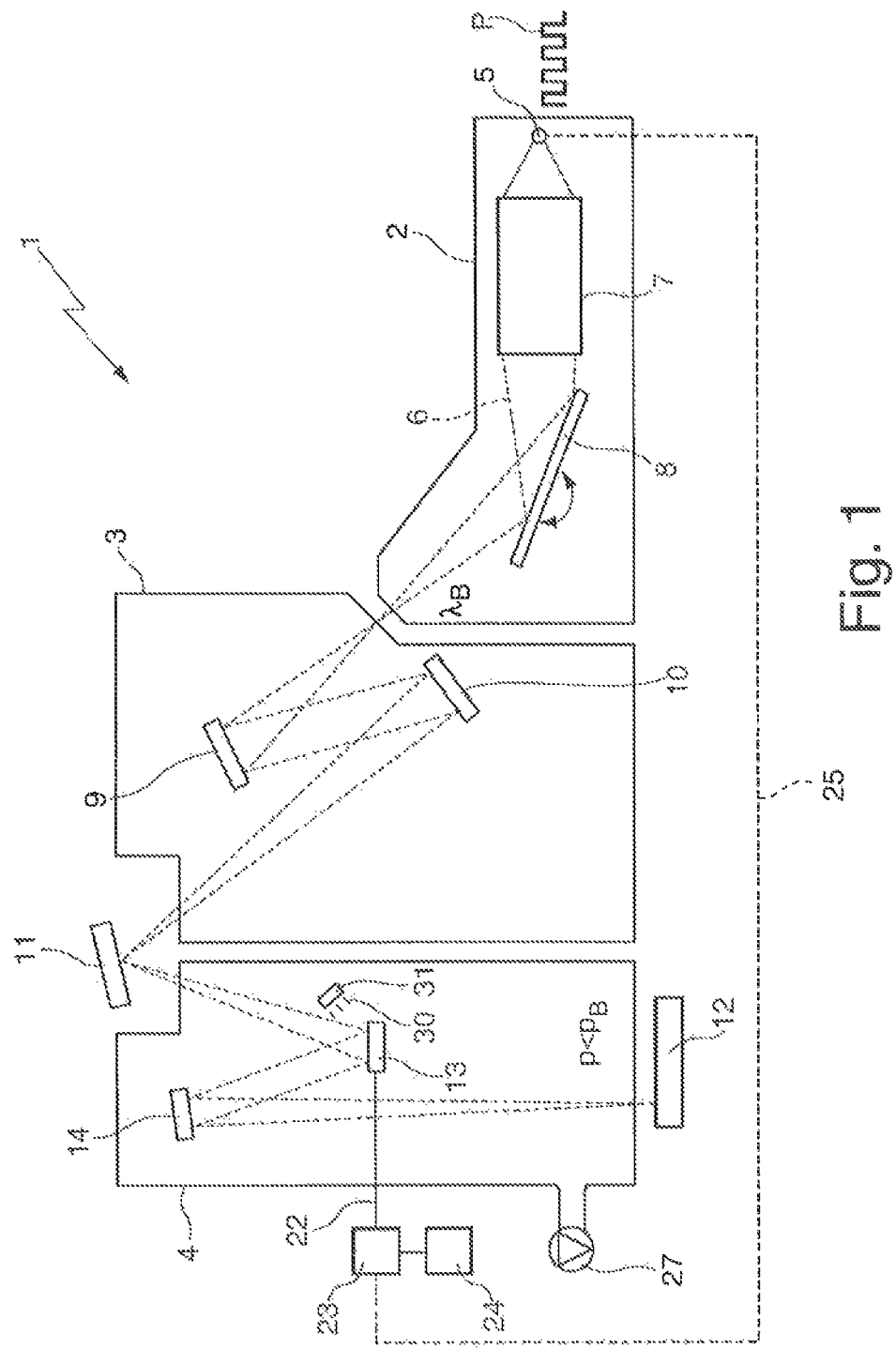
FIG. 1 shows a schematic illustration of an EUV lithography apparatus comprising a measuring device for measuring a photocurrent derived from an optical element.

FIG. 1 schematically shows an EUV lithography apparatus in the form of a projection exposure apparatus 1 for EUV lithography. The projection exposure apparatus 1 has a beam generating system 2, an illumination system 3 and a projection system 4, which are accommodated in separate vacuum housings and arranged successively in a beam path 6 proceeding from an EUV light source 5 of the beam shaping system 2. By way of example, a plasma source or a synchrotron can serve as the EUV light source 5. The radiation in the wavelength range of between approximately 5 nm and approximately 20 nm emerging from the light source 5 is firstly focused in a collimator 7. With the aid of a downstream monochromator 8, the desired operating wavelength $\lambda_B$, which is approximately 13.5 nm in the present example, is filtered out by variation of the angle of incidence, as indicated by a double-headed arrow. The collimator 7 and the monochromator 8 are embodied as reflective optical elements.

The radiation treated with regard to wavelength and spatial distribution in the beam generating system 2 is introduced into the illumination system 3, which has a first and second reflective optical element 9, 10. The two reflective optical elements 9, 10 direct the EUV radiation onto a photomask 11 as further reflective optical element, which has a structure that is imaged onto a wafer 12 on a reduced scale with the projection system 4. For this purpose, a third and fourth reflective optical element 13, 14 are provided in the projection system 4.

The reflective optical elements 9, 10, 11, 13, 14 each have a free interface which is exposed to the EUV radiation 6 from the light source 5. The optical elements 9, 10, 11, 13, 14 are operated under vacuum conditions in a residual gas atmosphere. Since the interior of the projection exposure apparatus 1 cannot be subjected to bake-out, the presence of residual gas constituents in the vacuum environment cannot be completely avoided, which constituents can deposit in the form of contaminations on the optical elements 9, 10, 11, 13, 14.

Figure 2:
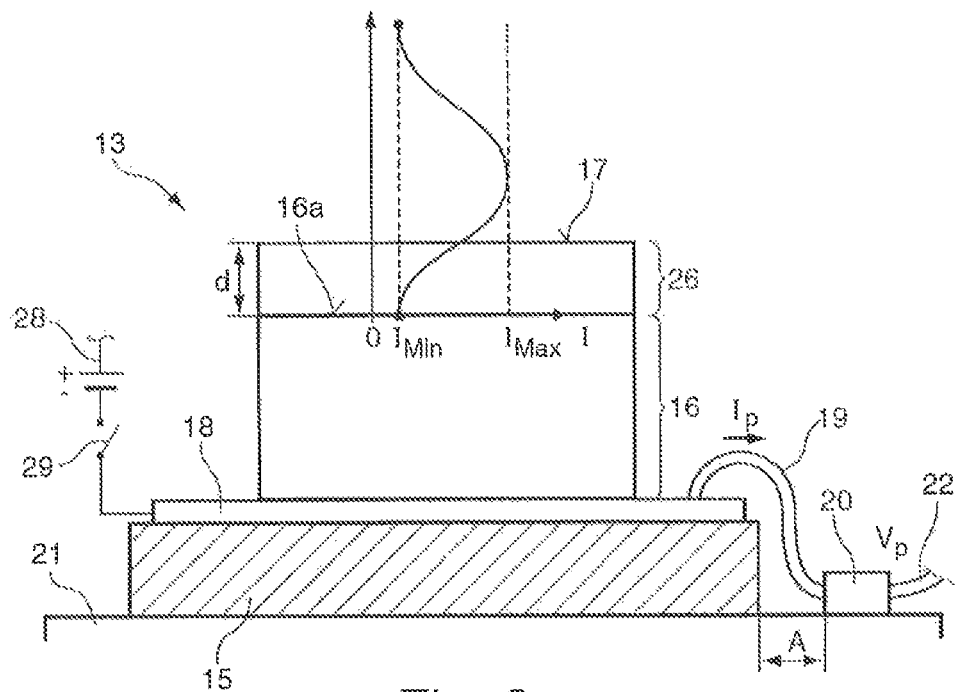
FIG. 2 shows an optical element of the EUV lithography apparatus from FIG. 1 with a contamination layer that has deposited on a multilayer coating and with a charge amplifier.

FIG. 2 shows an optical element 13 of the projection system 4 in a detail view. The optical element 13 has a substrate 15 composed of a material having a low coefficient of thermal expansion, which is typically less than 100 ppb/K at 22° C. or over a temperature range of approximately 5° C. to approximately 35° C. One material which has these properties is silicate or quartz glass doped with titanium dioxide and typically having a silicate glass proportion of more than 90%. One such silicate glass that is commercially available is sold by Corning Inc. under the tradename ULE® (Ultra Low Expansion glass). A further group of materials having a very low coefficient of thermal expansion is glass ceramics in which the ratio of the crystal phase to the glass phase is set in such a way that the coefficients of thermal expansion of the different phases virtually cancel one another out. Such glass ceramics are offered e.g. by Schott AG under the tradenames Zerodur®, or by Ohara Inc. under the tradename Clearceram®. The substrate 15 has a comparatively low electrical conductivity.

A reflective coating 16 is applied to the substrate 15, said reflective coating having a plurality of individual layers consisting of different materials. In the present example, the individual layers are formed alternately from materials having different refractive indices. If the operating wavelength $\lambda_B$ is approximately 13.5 nm as in the present example, then the individual layers usually consist of molybdenum and silicon. Other material combinations such as e.g. molybdenum and beryllium, ruthenium and beryllium or lanthanum and $B_4C$ are likewise possible.

The reflective multilayer coating 16 typically has a capping layer in order to prevent oxidation of the underlying individual layers. In the present example, the capping layer consists of ruthenium. Other materials, in particular metallic materials, such as rhodium, palladium, platinum, iridium, niobium, vanadium, chromium, zinc or tin, can also be used as capping layer materials.

In addition to the individual layers described, the reflective coating 16 can also comprise intermediate layers for preventing diffusion. The illustration of the individual layers, the auxiliary layers and the capping layer in the figures has been dispensed with in order to simplify the illustration. In the exemplary embodiment illustrated, the optical element 13 has a planar surface. That, too, was chosen thus only to simplify the illustration, that is to say that the optical element 13 can also have a curved surface form, wherein e.g. concave surface forms or convex surface forms are possible, which can be embodied both spherically and aspherically.

The materials of the (dielectric and/or metallic) individual layers of the reflective multilayer coating 16 have a comparatively high electrical conductivity in comparison with the substrate 15. It is therefore possible to derive a photocurrent $I_P$, which is generated during the EUV irradiation of the optical element 13 or its free interface 17 with the vacuum environment as a result of the photoelectric effect or via secondary electrons, at an electrically conductive layer 18 arranged between the reflective multilayer coating 16 and the substrate 15. For this purpose, the electrically conductive layer 18 projects laterally beyond the multilayer coating 16 and the photocurrent $I_P$ can be connected to a line 19 for example via a soldering point or the like and can be carried away via said line. In the present example, the line 19 leads to a signal input of a charge amplifier 20, which is fixed to a mount 21 for the optical element 13. The charge amplifier 20, which is embodied as an operational amplifier in the present example, converts the incoming photocurrent $I_P$ into an output voltage $V_P$ which is proportional to said photocurrent and amplified by the proportionality factor.

The output voltage $V_P$ is fed via a measuring line 22 to a voltage measuring device 23, which is illustrated in FIG. 1 and which, in the present example, is arranged outside the vacuum environment formed in the projection system 4. This is possible since the transmission of the output voltage $V_P$ generated at the output of the charge amplifier 20 via the measuring line 22 is possible without any problems even over relatively large distances. By contrast, the line 19 for the photocurrent $I_P$ derived from the optical element 13 should be chosen not to be too long, that is to say that the charge amplifier 20 should not be arranged too far away from the optical element 13, wherein the distance should typically be less than 150 cm, in particular less than approximately 50 cm. In the example shown in FIG. 2, the distance A is approximately 5 cm. Not only the distance A but also the line 19 connecting the optical element 13 to the charge amplifier 20 should be as short as possible.

The EUV light source 5 from FIG. 1 is operated in a pulsed manner, that is to say that light pulses P are generated which are interrupted by pulse intermissions. In order to determine the photocurrent $I_P$ during the irradiation with EUV radiation 6, i.e. during a respective EUV pulse P (but generally not between the pulses P), the measuring device 23 is connected to the EUV light source 5 via a signal line 25, which supplies a trigger signal or a reference signal to the measuring device 23, in order to read out the output voltage $V_P$ supplied by the charge amplifier 20 synchronously with the EUV pulses P (lock-in method). The voltage measuring device 23 thus supplies the photocurrent $I_P$, to put it more precisely a voltage value proportional thereto, during a respective EUV pulse P.

The measured photocurrent $I_P$ (or the voltage $V_P$ proportional thereto and forming a measure of the photocurrent $I_P$) is fed to an evaluation device 24, which is likewise shown in FIG. 1. A plurality of characteristic curves between the measured photocurrent $I_P$ and the thickness d of a contamination layer 26 grown onto the reflective multilayer coating 16, said contamination layer being shown in FIG. 2, are stored in the evaluation device 24. The contamination layer 26 is produced by virtue of the fact that contaminating substances, the presence of which in the residual gas atmosphere in which the optical elements 13, 14, . . . are operated cannot be completely avoided, deposit on the optical elements 13, 14, . . . , this typically being fostered by EUV irradiation. The deposited contaminating substance is often carbon, but the contamination layer 26 can also contain other contaminating substances or be formed therefrom.

FIG. 2 likewise illustrates the field intensity I of the electric field strength of a standing wave that forms during the irradiation with the EUV radiation 6 at the free interface 17 or in the underlying multilayer coating 16 of the optical element 13. As can likewise be discerned in FIG. 2, the field intensity I fluctuates between a minimum value $I_{Min}$ (node) and a maximum value $I_{Max}$ (antinode). The distance between two nodes of the standing wave in this case corresponds to half the operating wavelength $\lambda_B$ of the EUV radiation 6, i.e. in the present case approximately 6.75 nm. As can readily be discerned in FIG. 2, the value of the field intensity I at the free interface 17 varies depending on the thickness d of the contamination layer 26. The field strength I at the free interface 17 in this case influences the intensity of the photocurrent $I_P$ generated during the irradiation, wherein said photocurrent is typically all the greater, the greater the field strength I at the interface 17.

The relationship or the characteristic curve between the measured photocurrent $I_P$ and the thickness d of the contamination layer 26 can be measured e.g. during the production of the EUV lithography apparatus 1, wherein if appropriate the reflectivity of the optical element 13 is additionally determined. In the installed state, by contrast, the reflectivity of an individual optical element typically can no longer be determined. However, the transmission of the entire EUV lithography apparatus 1 and thus the product of the reflectivities of the individual optical elements can be determined. The $I_P/d$ characteristic curve is dependent on the absolute value of the EUV radiation 6 impinging on the free interface 17, which is dependent on the illumination settings set in the illumination system 3, and on the structure on the mask 11 to be imaged. In the evaluation device 24, a corresponding $I_P/d$ characteristic curve can be stored for each of the types of illumination that can be set at the illumination system 3 (e.g. dipole illumination, quadrupole illumination, annular illumination, etc.). Correspondingly, a respective $I_P/d$ characteristic curve can also be stored for respectively different masks 11, since these likewise influence the intensity distribution in the projection system 4.

Figure 3:
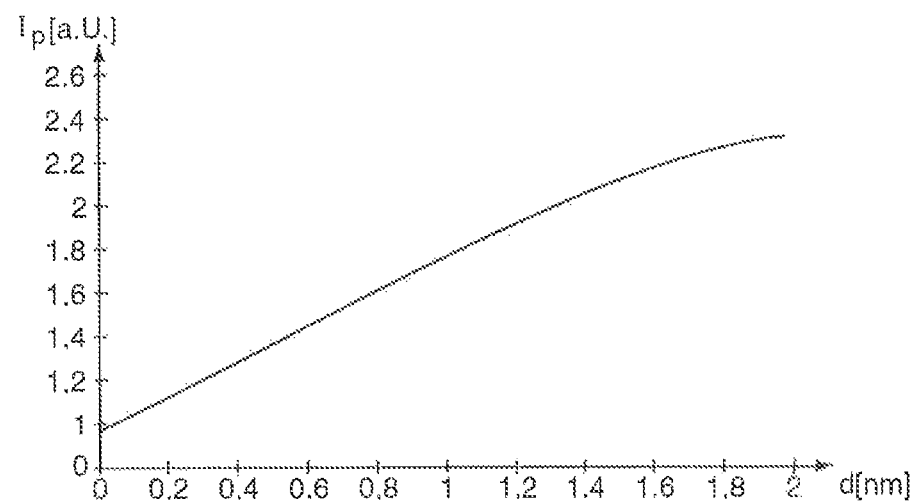
FIG. 3 shows a photocurrent/thickness curve for determining the thickness of the contamination layer of FIG. 2.

The evaluation device 24 selects the suitable $I_P/d$ characteristic curve on the basis of the chosen illumination setting and, if appropriate, on the basis of the chosen photomask 11. One example of such a characteristic curve is shown in FIG. 3. The characteristic curve shown rises strictly monotonically over a thickness range of between 0 nm and 2 nm of the contamination layer 26, such that a unique assignment of a value for the sample current $I_P$ to the thickness d of the contamination layer 26 is possible, such that the latter is uniquely determinable from the measured sample current $I_P$. Since the electrically conductive layer 18 extends below the entire multilayer coating 16, the charges generated at all locations of the free interface 17 are measured as photocurrent $I_P$. Since the measured photocurrent $I_P$ covers all locations at the free interface 17, it is generated from the entire angle-of-incidence distribution of the EUV radiation 6 at the free interface 17 or at the multilayer coating 16. The measured photocurrent $I_P$ also covers the entire wavelength band of the EUV radiation 6 reflected at the multilayer coating 16, i.e. in the present case a narrow wavelength range around the operating wavelength $\lambda_B$ of 13.5 nm. In the example shown in FIG. 2 it was assumed that the contamination layer 26 has a thickness d which is constant over the free interface 17. The contamination layer 26 can have a thickness d which varies in a location-dependent manner over the free interface 17, such that the thickness d measured in the manner described above has a mean value. In order to make a statement about the thickness d of the contamination layer 26 at different locations of the free interface 17, those parameters of the EUV lithography apparatus 1 which have an influence on the local distribution of the intensity of the EUV radiation 6 impinging on the free interface 17 can be varied in a targeted manner. Said parameters are substantially the illumination settings of the illumination system 3 and/or the structures formed on the mask 11. On the basis of the intensity distribution—known for predefined operating parameters—of the EUV radiation 6 at the free interface 17, it is possible to examine, in a targeted manner, the thickness d of the contamination layer 26 in a region at which the intensity I of the impinging EUV radiation 6 is particularly high. By way of example, as a result of the setting of an annular illumination at the illumination system 3, it is possible to examine, in a targeted manner, the thickness d of the contamination layer 26 in a ring-shaped region of the optical element 13 if the latter is arranged in proximity to a pupil plane.

Generally, no exposure operation is possible during such variation of the operating parameters of the EUV lithography apparatus 1. In this case, the EUV lithography apparatus 1 is advantageously switched to measurement operation.

Besides the determination of the thickness d of the contamination layer 26, with the aid of the construction described above it is also possible to determine the phase angle $\phi_G$ (or $\phi_G$-$\phi_{G*}$) at the free interface 17. The considerations above assumed that the phase angle at the top side 16a of the multilayer coating 16 does not vary, that is to say that in FIG. 2, by way of example, a node is permanently formed at the top side 16a of the multilayer coating 16. The information about the phase angle at the top side 16a of the multilayer coating 16 can be obtained e.g. by measurement of the optical element 13 prior to installation in the EUV lithography apparatus 1 or, if appropriate, by simulations.

In the course of the service life of the optical element 13, however, the state of the multilayer coating 16 can vary on account of the irradiation with EUV radiation 6 or e.g. on account of diffusion mechanisms, etc. By way of example, the multilayer coating 16 can experience compaction, with the result that its thickness decreases, or the ratio between the proportion of high refractive index material and the proportion of low refractive index material (also designated as gamma value) and thus the structure of the multilayer coating 16 can vary as a result of a diffusion between the individual layers. Such variations lead to a change in the phase angle at the top side 16a of the multilayer coating 16.

Figure 4:
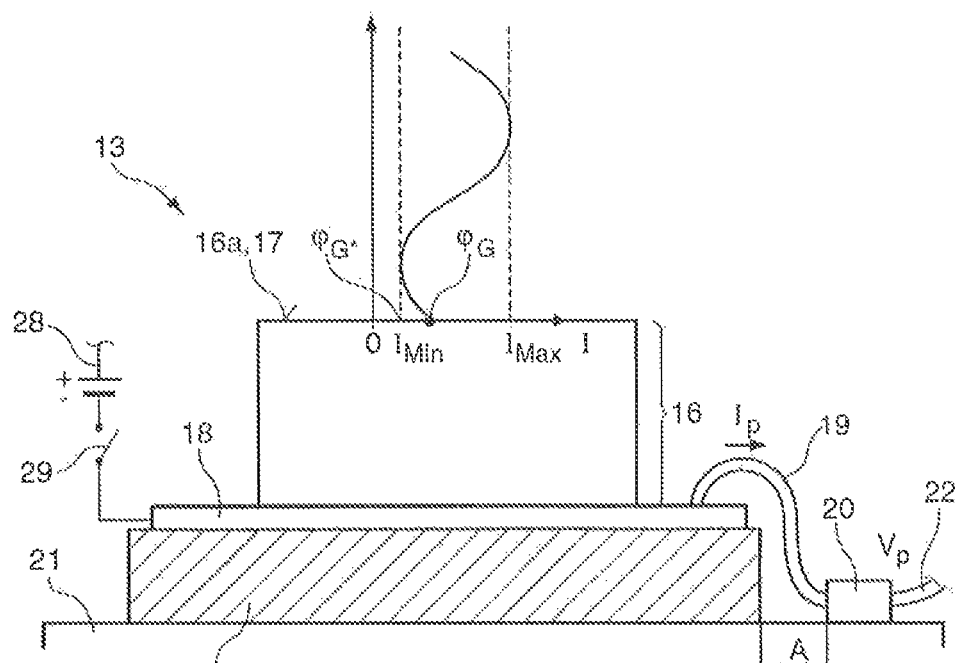
FIG. 4 shows an optical element having a free interface formed at a multilayer coating of the optical element.

In order to be able to detect such slow structural variations of the multilayer coating 16, it is generally necessary to remove the contamination layer 26 so that the free interface 17 is formed at the top side 16a of the multilayer coating 16, as is the case for the optical element 14 shown in FIG. 4. In this case, the contamination layer 26 can be removed from the multilayer coating 16 with the aid of cleaning methods which are familiar to the person skilled in the art and which are not described in greater detail here, for example by the use of a reactive gas, in particular with the aid of activated hydrogen.

Figure 5:
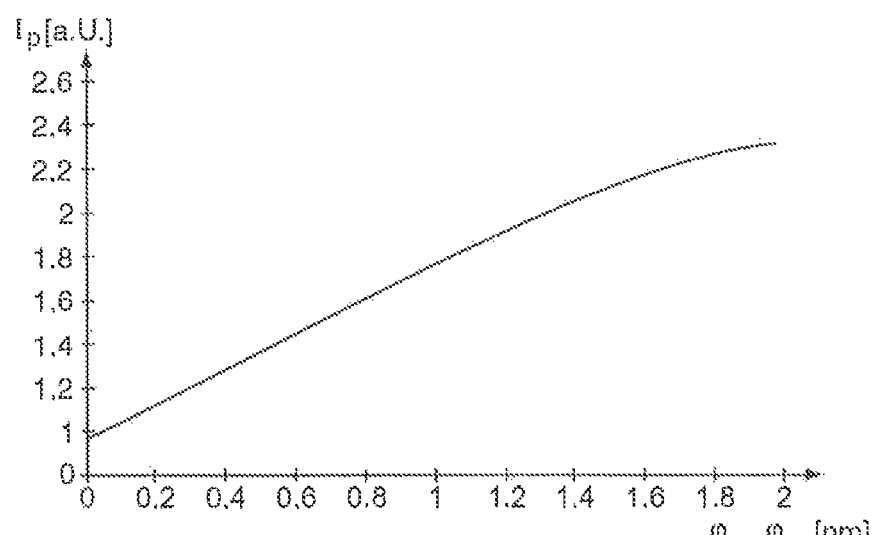
FIG. 5 shows a photocurrent/phase curve for determining the phase angle at the free interface of the optical element of FIG. 4.

If a contamination layer is no longer present on the multilayer coating 16, the phase angle (PG at the free interface 17 can be compared directly with the nominal phase angle $\phi_{G*}$, which, at the point in time of providing the optical element 14, was present there or was supposed to be present there. In the present example, it is assumed that the phase angle $\phi_{G*}$ upon the provision of the optical element 14 had a node at the free interface 17 (cf. FIG. 2). In this case, the field intensity I has an intensity minimum $I_{Min}$ at the free interface 17 and the associated photocurrent $I_P$ is minimal. As can be discerned in FIG. 5, in this case the profile of the characteristic curve between the photocurrent $I_P$ and the phase difference $\phi_G$-$\phi_{G*}$ (also designated as (relative) phase angle) corresponds to that during the growth of the contamination layer 26 (cf. FIG. 3).

The above-described possibility of determining the thickness d of the contamination layer 26 in a location-dependent manner can analogously also be applied to the determination of the phase angle or the phase difference $\phi_G$-$\phi_{G*}$. The phase angle $\phi_G$-$\phi_{G*}$ enables a characterization of the state of the optical element 14 or of the reflective multilayer coating 16 thereof over the service life thereof (see above). Moreover, it is possible to determine the (relative) phase angle at different optical elements 13, 14, . . . of the EUV lithography apparatus 1 in order to make statements about the imaging properties thereof.

On the basis of the sample current measurement alone it is generally not possible to distinguish between a grown contamination layer 26 and a variation of the phase angle $\phi_G$-$\phi_{G*}$ as a result of effects such as compaction or other alterations of the reflective multilayer coating 16. In order to make a distinction between the two effects, besides the complete removal of the contamination layer 26 it is also possible, if appropriate, to use further measuring methods, for example the measurement of the total reflectivity and/or total transmission of the EUV lithography apparatus 1 for the EUV radiation 6, which permits conclusions to be drawn regarding the magnitude of the (total) thickness of the contamination layers on all the reflective optical elements.

In order to enable the thickness d and/or the phase angle $\phi_G$-$\phi_{G*}$ to be measured as precisely as possible, from time to time a check should be made to determine whether the predefined relationship between the photocurrent $I_P$ and the thickness d and/or the phase angle $\phi_G$-$\phi_{G*}$ is still correct. A variation of this relationship can arise, if appropriate, from a varying contact resistance when tapping off the photocurrent $I_P$, which corrupts the measurement result. The calibration is typically carried out in the operating pauses of the EUV lithography apparatus 1, that is to say at a point in time at which no EUV irradiation of the optical elements 13, 14, . . . takes place.

For the calibration, it is possible to use a charge standard shown in FIG. 2 in the form of a capacitor 28, which, for the calibration, with the aid of a switch 29, is connected to the optical element 13, to put it more precisely to the conductive layer 18, and is discharged in this case. Since the capacitance of the capacitor 28 is known, a defined number of charges or a defined photocurrent $I_P$ is fed to the charge amplifier 20. If the photocurrent $I_P$ measured by the measuring device 23 deviates from a reference value stored in the evaluation device 24, this is an indication that the measurement is no longer functioning correctly. On the basis of the measurement result, the predefined relationship or the characteristic curve can be modified in a targeted manner, such that it generates a corrected value for the thickness d and/or the phase angle $\phi_G$-$\phi_{G*}$ during the measurement.

Alternatively or additionally, the calibration can be carried out by calibration radiation 30 from a calibration radiation source 31 being fed to the optical element, as is shown in FIG. 1. In this case, the calibration radiation 30 lies outside the wavelength range reflected by the multilayer coating 16. In the example shown, a laser diode having a wavelength of 440 nm (i.e. blue) is used as the calibration light source 31. However, it is also possible to use other, in particular broadband, calibration light sources 31, which preferably generate radiation in the UV range or in the deep UV range. In contrast to the illustration in FIG. 1, the calibration radiation 30 can also be fed to the optical element 13 with the aid of an optical fiber (not shown).

If appropriate, the EUV light source 5 itself can also serve as the calibration light source, if, with the aid of the monochromator 8, the selected wavelength is detuned in a targeted manner relative to the operating wavelength $\lambda_B$ and is shifted e.g. into a wavelength range of between approximately 9 nm and approximately 11 nm or between approximately 14 nm and approximately 16 nm. Instead of the monochromator, it is also possible to use an optical filter which filters wavelengths in the range of between approximately 11 nm and approximately 14 nm. Since only wavelengths in the range of between approximately 11 nm and approximately 14 nm are typically reflected at the optical elements 9 to 11, 13, 14, a dedicated beam guiding optical unit is required, if appropriate, for feeding the calibration radiation to the respective optical element. In the present case the calibration does not have to be carried out during an operating pause, but rather with the EUV light source 5 activated. As a result of a predefined radiation dose of the calibration radiation 30 being fed to the optical element 13, a defined number of charges are generated, and so the calibration can be carried out as described above in connection with the charge standard 28.

To summarize, in the manner described above, the thickness d of a contamination layer 26 and/or the phase angle $\phi_G$-$\phi_{G^*}$ can be determined during the exposure operation of the EUV lithography apparatus 1. Moreover, according to the invention, any additional or even all the optical elements 13, 14, . . . of the EUV lithography apparatus 1 can be measured in the manner described above during exposure operation and/or in a measurement operation mode provided specifically for the photocurrent measurement.

What is claimed is:

1. An extreme ultraviolet (EUV) lithography apparatus, comprising:
    at least one optical element, having a substrate and a multilayer coating that reflects EUV radiation, and an electrical contact with the optical element, to derive a photocurrent generated in response to irradiation of the optical element with the EUV radiation,
    a charge amplifier in contact with the optical element and configured to supply an output voltage in accordance with the photocurrent,
    a measuring device configured to measure the photocurrent in accordance with the output voltage supplied by the charge amplifier,
    a pulsed EUV light source, and
    an evaluation device, configured to determine a phase angle at a free interface of the optical element and/or a thickness of a contamination layer formed on the multilayer coating in accordance with a predefined relationship between the phase angle and/or the thickness and the measured photocurrent, wherein the measured photocurrent is generated from an entire wavelength and angle-of-incidence distribution of the EUV radiation impinging on the multilayer coating.

2. The EUV lithography apparatus according to claim 1, wherein the charge amplifier is arranged at a distance of less than 150 cm from the optical element.

3. The EUV lithography apparatus according to claim 1, further comprising: a charge standard configured to feed a predefined number of charges to the optical element.

4. The EUV lithography apparatus according to claim 1, further comprising: a calibration light source configured to irradiate the optical element with calibration radiation at wavelengths that are not reflected by the multilayer coating.

5. The EUV lithography apparatus according to claim 4, wherein the calibration light source is configured to generate calibration radiation at extreme ultraviolet wavelengths of between 9 nm and 11 nm or between 14 nm and 16 nm or at ultraviolet wavelengths of between 190 nm and 450 nm.

6. The EUV lithography apparatus according to claim 1, wherein the measuring device is configured to read out the output voltage supplied by the charge amplifier synchronously with pulses of the EUV light source.

* * * * *

UNITED STATES PATENT AND TRADEMARK OFFICE
CERTIFICATE OF CORRECTION

PATENT NO. : 9,618,387 B2
APPLICATION NO. : 14/808637
DATED : April 11, 2017
INVENTOR(S) : Michael Gerhard Page 1 of 1

It is certified that error appears in the above-identified patent and that said Letters Patent is hereby corrected as shown below:

In the Specification

Column 11, Line 52 Delete "(PG" and insert -- φG --, therefor.

Signed and Sealed this
Third Day of September, 2019

Andrei Iancu
*Director of the United States Patent and Trademark Office*